US010485402B2

(12) United States Patent
Tanaka et al.

(10) Patent No.: US 10,485,402 B2
(45) Date of Patent: Nov. 26, 2019

(54) OBSERVATION SYSTEM

(71) Applicant: OLYMPUS CORPORATION, Tokyo (JP)

(72) Inventors: Yoshinori Tanaka, Hino (JP); Takeshi Ito, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 409 days.

(21) Appl. No.: 15/398,044

(22) Filed: Jan. 4, 2017

(65) Prior Publication Data

US 2017/0112360 A1    Apr. 27, 2017

Related U.S. Application Data

(63) Continuation of application No. PCT/JP2015/068214, filed on Jun. 24, 2015.

(30) Foreign Application Priority Data

Jul. 10, 2014    (JP) ................... 2014-142631

(51) Int. Cl.
     *A61B 1/00*         (2006.01)
     *G01B 11/24*       (2006.01)
     (Continued)

(52) U.S. Cl.
     CPC ........ *A61B 1/00096* (2013.01); *A61B 1/0002* (2013.01); *A61B 1/0005* (2013.01);
     (Continued)

(58) Field of Classification Search
CPC combination set(s) only.
See application file for complete search history.

(56) References Cited

U.S. PATENT DOCUMENTS

| 4,827,909 A | 5/1989 | Kato et al. |
| 6,031,941 A * | 2/2000 | Yano ............... G06T 7/571 |
| | | 382/154 |

(Continued)

FOREIGN PATENT DOCUMENTS

| CN | 101530313 A | 9/2009 |
| JP | S63-242233 A | 10/1988 |

(Continued)

OTHER PUBLICATIONS

Chinese Office Action dated Sep. 10, 2018 in Chinese Patent Application No. 201580037611.6.

(Continued)

*Primary Examiner* — John P Leubecker
*Assistant Examiner* — Shankar Raj Ghimire
(74) *Attorney, Agent, or Firm* — Scully, Scott, Murphy & Presser, et al.

(57) ABSTRACT

The observation system images a specimen under illumination lights applied at different timings through irradiation windows arranged near one image sensor, generates optical information included in each image, calculates values of light volumes included in the optical information output from identical-point originated pixels, which have imaged an identical point as the same characteristic point on the specimen, in the respective pixels as a relative distance from an image sensor, compares the optical information between the pixels, and determines the identical point on the specimen as a flat surface portion or an inclined portion on the basis of a comparison result, associates the distance with the flat surface portion or the inclined portion, estimates a surface shape of the specimen, and displays a three-dimensional image of the specimen.

14 Claims, 9 Drawing Sheets

(51) Int. Cl.
  *A61B 1/045* (2006.01)
  *A61B 1/05* (2006.01)
  *A61B 1/06* (2006.01)
  *A61B 1/07* (2006.01)
  *A61B 1/04* (2006.01)
  *G01C 3/08* (2006.01)

(52) U.S. Cl.
  CPC ...... *A61B 1/00006* (2013.01); *A61B 1/00009* (2013.01); *A61B 1/043* (2013.01); *A61B 1/045* (2013.01); *A61B 1/05* (2013.01); *A61B 1/0607* (2013.01); *A61B 1/0653* (2013.01); *A61B 1/0676* (2013.01); *A61B 1/07* (2013.01); *G01B 11/24* (2013.01); *G01C 3/08* (2013.01)

(56) References Cited

U.S. PATENT DOCUMENTS

| | | | | |
|---|---|---|---|---|
| 7,747,151 | B2* | 6/2010 | Kochi | G01B 11/24 348/50 |
| 2001/0014171 | A1* | 8/2001 | Iijima | G06T 7/55 382/154 |
| 2003/0021381 | A1* | 1/2003 | Koppe | G06T 7/33 378/163 |
| 2005/0237581 | A1* | 10/2005 | Knighton | G01B 11/24 358/473 |
| 2009/0227837 | A1* | 9/2009 | Shimizu | A61B 1/00009 600/109 |
| 2010/0048995 | A1* | 2/2010 | Suijver | A61B 1/00167 600/111 |
| 2011/0025827 | A1* | 2/2011 | Shpunt | G01B 11/22 348/47 |
| 2012/0316396 | A1 | 12/2012 | Robertson | |
| 2015/0348311 | A1* | 12/2015 | Saur | G06T 7/593 382/128 |
| 2016/0217591 | A1* | 7/2016 | Krupnik | G06T 7/60 |
| 2016/0278678 | A1* | 9/2016 | Valdes | A61B 5/14556 |

FOREIGN PATENT DOCUMENTS

| | | |
|---|---|---|
| JP | H05-211996 A | 8/1993 |
| JP | H06-076888 A | 3/1994 |
| JP | 2000-136913 A | 5/2000 |
| JP | 2003-093336 A | 4/2003 |
| JP | 2007-322357 A | 12/2007 |
| JP | 2009-213627 A | 9/2009 |
| JP | 2012-050650 A | 3/2012 |
| JP | 2013-063179 A | 4/2013 |

OTHER PUBLICATIONS

Japanese Office Action dated Jun. 12, 2018 in Japanese Patent Application No. 2014-142631.
International Search Report dated Sep. 29, 2015 issued in PCT/JP2015/068214.
English translation of International Preliminary Report on Patentability dated Jan. 19, 2017 together with the Written Opinion in related International Application No. PCT/JP2015/068214.

* cited by examiner

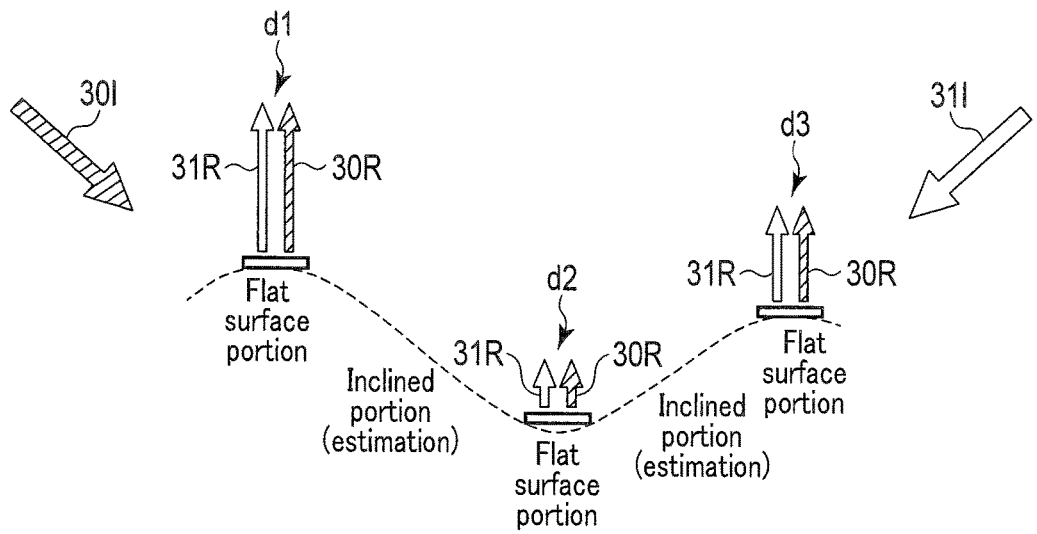
F I G. 5
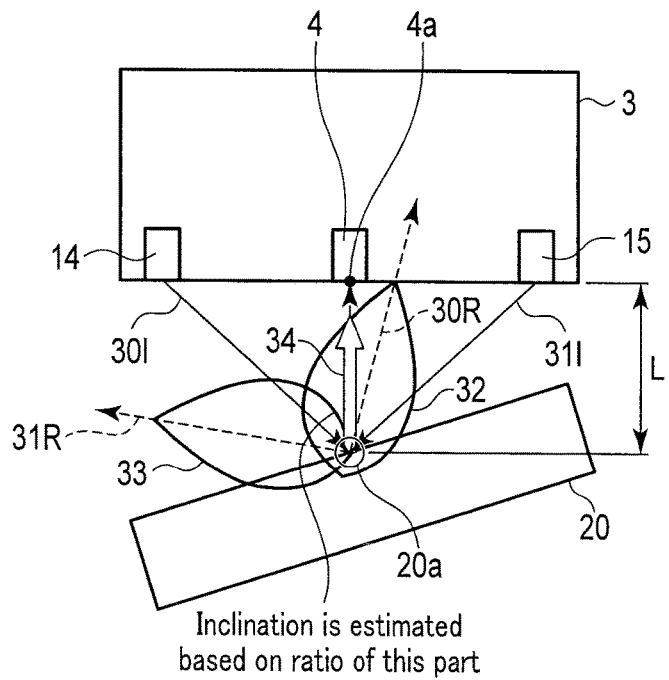
Inclination is estimated based on ratio of this part
F I G. 6

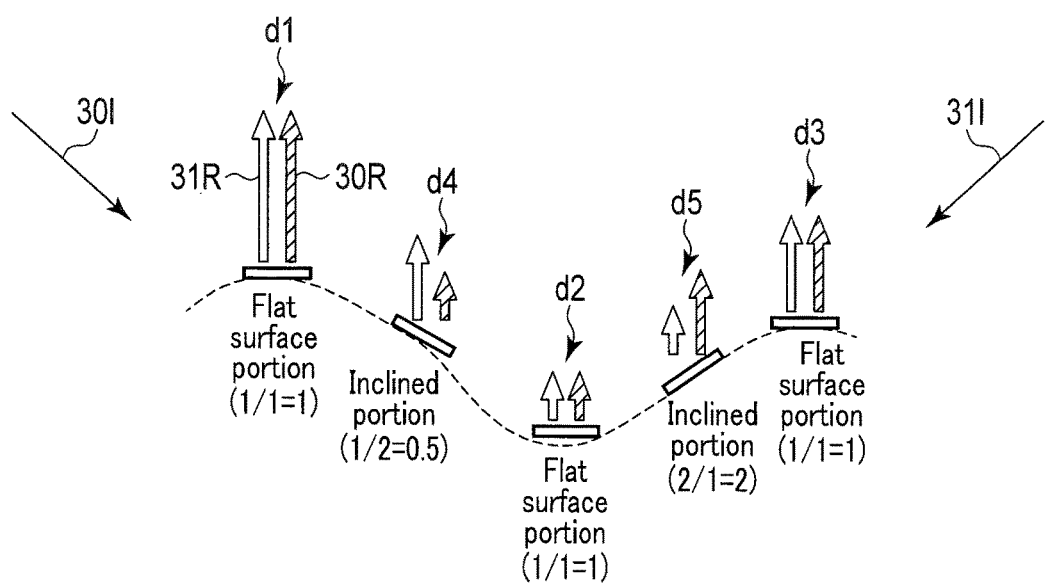
F I G. 7

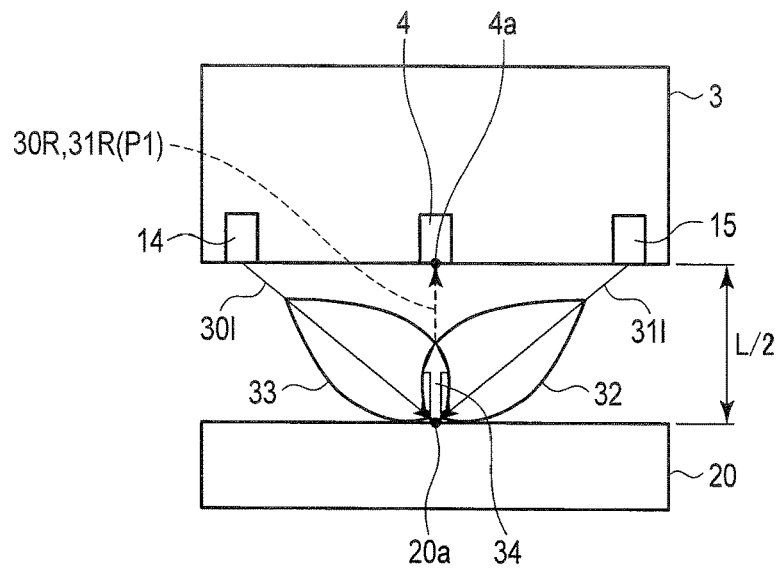
F I G. 11
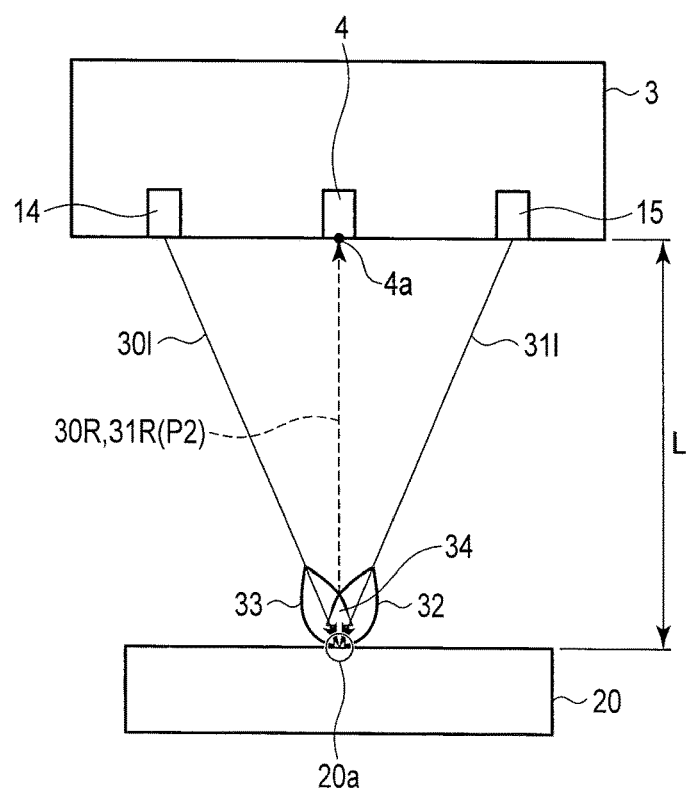
F I G. 12

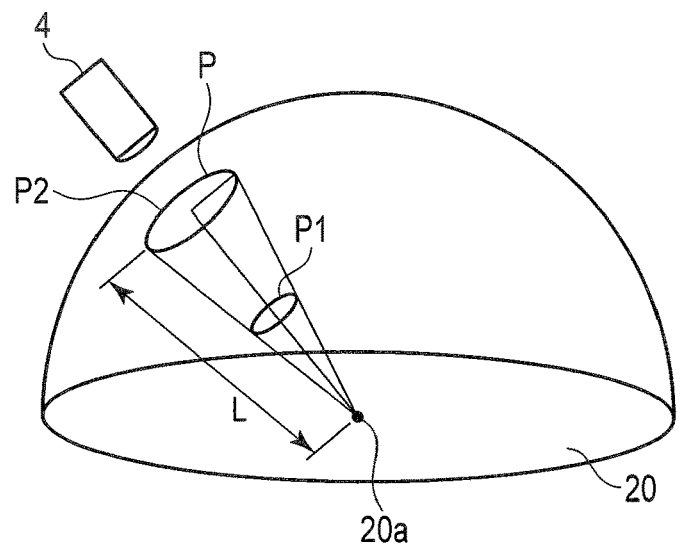
F I G. 13
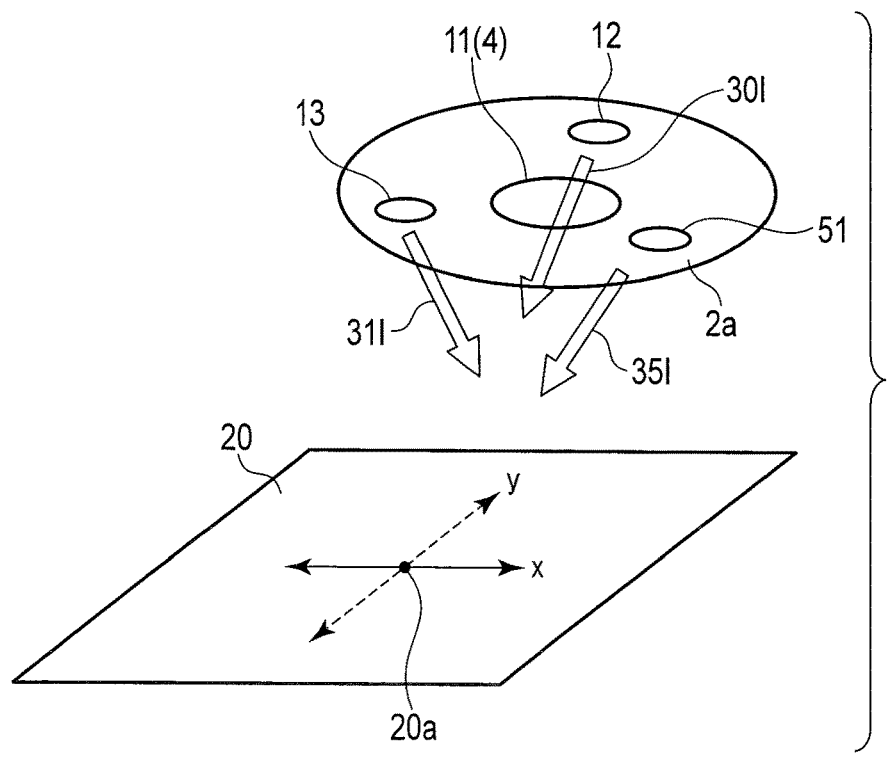
F I G. 14

OBSERVATION SYSTEM

CROSS-REFERENCE TO RELATED APPLICATIONS

This is a Continuation application of PCT Application No. PCT/JP2015/068214, filed Jun. 24, 2015, which was published under PCT Article 21(2) in Japanese. This application is based upon and claims the benefit of priority from prior the Japanese Patent Application No. 2014-142631, filed Jul. 10, 2014 the entire contents of which are incorporated herein by references.

BACKGROUND OF THE INVENTION

1. Field of the Invention

The present invention relates to an observation system which estimates a surface shape of a specimen based on perspective information calculated from each captured image provided by emitting lights to the same observing position on a specimen more than once, and displays it as a stereoscopic image.

2. Description of the Related Art

Generally, when displaying a stereoscopic image (a three-dimensional image) on a monitor, two imaging systems having a difference in viewpoint (a binocular parallax) are used, and respective captured images are combined and displayed. In an observation apparatus applied to an endoscope or the like having an image sensor mounted therein, at the time of conducting an endoscopic operation using an arm having a treatment tool disposed thereto, three-dimensional display to stereoscopically display an irregular state of a surface of a specimen as a treatment target in an easy-to-understand manner is desired.

It is known than perspective information required to display the irregular state of the specimen surface is acquired by using a so-called triangulation system of, for example, applying light to a measurement position, taking the reflected light into an image sensor, and calculating the perspective information as a distance from an image forming position on a light receiving surface to an observing position, and that the irregular state of the observing position can be calculated from this perspective information.

However, in the observation system in an endoscope or the like, a decrease in diameter of an inserting section is desired, a forceps hole and others are formed in a distal end surface of this section, an arrangement space where imaging optical systems (compound eyes) are arranged is not provided, and hence configuring a three-dimensional image by one imaging optical system is desired. For example, Patent Literature 1: Jpn. Pat. Appln. KOKOKU Hei 6-76888 proposes a measurement method of moving one light source to one imaging optical system so that diffusion lights having the same luminous intensity are applied to an immovable observing position from different positions respectively, measuring a luminance distribution of acquired captured images, calculating a distance distribution of surfaces of measurement positions, and measuring an irregular state of the observing position. Here, a distance from the light source to the observing position surface is calculated based on the fact that the luminance is in inverse proportion to a square of a distance from the light source to each measurement position, and the distance distribution is calculated from the luminance distribution provided by reflected lights.

The observation system according to the present invention acquires perspective information which suggests an irregular state of a specimen surface from captured images captured under illumination lights sequentially applied at continuous timings through irradiation windows at different positions aligned in one imaging optical system, and displays a three-dimensional observation image based on the perspective information.

Furthermore, the observation system images a specimen under illumination lights applied at different timings through irradiation windows arranged near one image sensor, generates optical information included in each image, calculates values of light volumes included in the optical information output from identical-point originated pixels, which have imaged an identical point as the same characteristic point on the specimen, in the respective pixels as a relative distance from an image sensor, compares the optical information between the pixels, and determines the identical point on the specimen as a flat surface portion or an inclined portion on the basis of a comparison result, associates the distance with the flat surface portion or the inclined portion, estimates a surface shape of the specimen, and displays a three-dimensional image of the specimen.

BRIEF SUMMARY OF THE INVENTION

According to an embodiment of the present invention, there is provided an observation system comprising: a light source apparatus comprising a first irradiation window through which first illumination light is applied, and a second irradiation window through which second illumination light is applied; and an image sensor which captures images of a specimen irradiated with the first and second illumination lights, wherein the light source apparatus comprises a light emission controller which emits the first illumination light and the second illumination light at different timings, the first and second illumination lights have substantially equal optical characteristics, wherein the image sensor is configured to acquire: a first image which is an image of the specimen provided by the first illumination light alone; and a second image which is an image of the specimen provided by the second illumination light alone, the first image includes first optical information and the second image includes second optical information, respectively, and wherein the observation system comprises: an optical information recorder which records the first optical information and the second optical information; and an identical-point originated pixel extracting circuit which compares the first image with the second image, associates a first image identical-point originated pixel as an identical-point originated pixel in the first image and a second image identical-point originated pixel as an identical-point originated image in the second image, which are originated from an identical point on the specimen, with each other, and extracts a first identical point and a second identical point as identical points on the specimen, an arithmetic circuit which compares first optical information of a first image first identical-point originated pixel at the first identical point with second optical information of a second image first identical-point originated pixel at the same, compares first optical information of a first image second identical-point originated image at the second identical point with second optical information of a second image second identical-point originated pixel at the same, and calculates specimen perspective information which is a relative distance relationship of the first identical point and the second identical point on the specimen from the image sensor; a surface shape estimating section which estimates a surface shape of the specimen from the specimen perspective information; and a display which displays a stereoscopic image to which the surface shape estimated by the surface shape estimating section is reflected.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 5 is a view conceptually showing heights based on reflected light volumes from flat surfaces when first illumination light and second illumination light are applied to the specimen;

FIG. 6 is a view showing a relationship between light volumes in two reflected lights when a distal end surface of an inserting section faces a surface of the specimen at a slant;

FIG. 7 is a view conceptually showing inclinations of the surface of the specimen based on ratios of the reflected light volumes of the first illumination light and the second illumination light;

FIG. 11 is a view showing a conceptual arrangement example of an observation system according to a second embodiment;

FIG. 12 is a view showing a conceptual arrangement example of acquiring specimen perspective information from illumination lights in a state where the observation system is away from the specimen at a distance L;

FIG. 13 is a conceptual view for explaining a relationship between a distance and a light receiving amount;

FIG. 14 is a conceptual view of an image including an identical point for explaining characteristics of an observation system according to a third embodiment.

DETAILED DESCRIPTION OF THE PREFERRED EMBODIMENT

Embodiments according to the present invention will now be described hereinafter in detail with reference to the drawings.

First Embodiment

Figure 1:
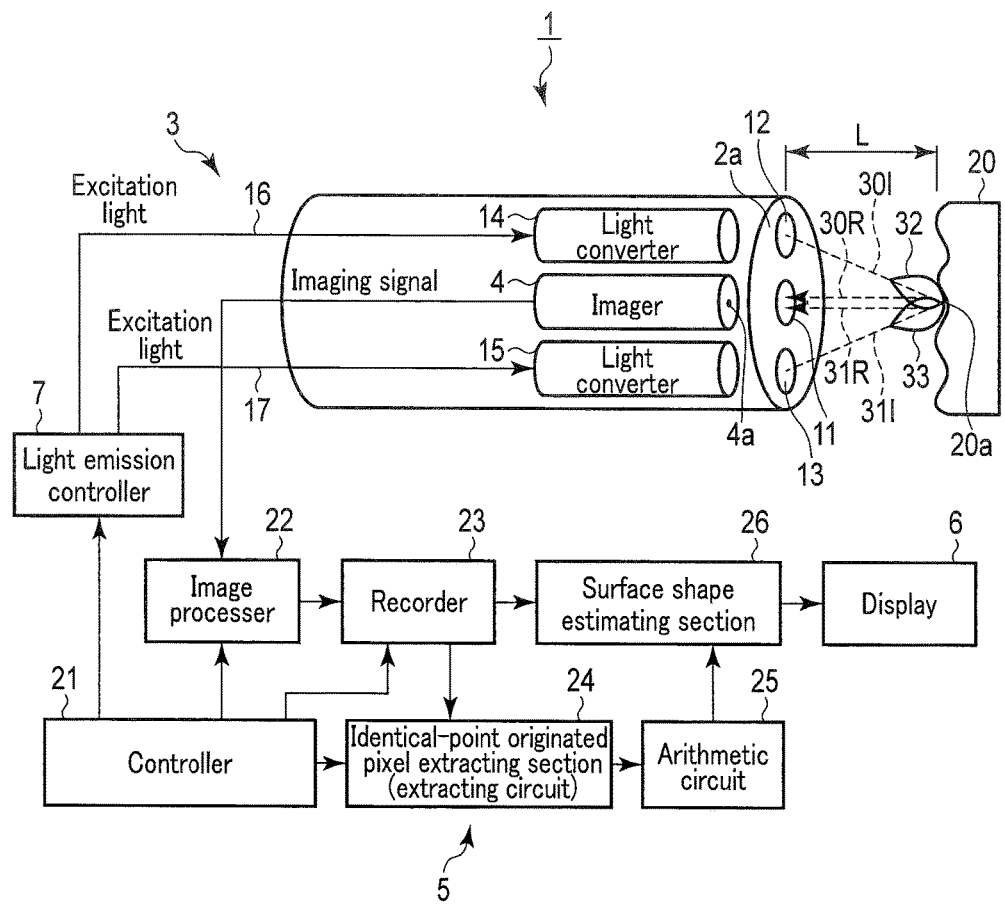
FIG. 1 is a view showing an entire configuration of an observation system according to a first embodiment of the present invention.
Figure 2:
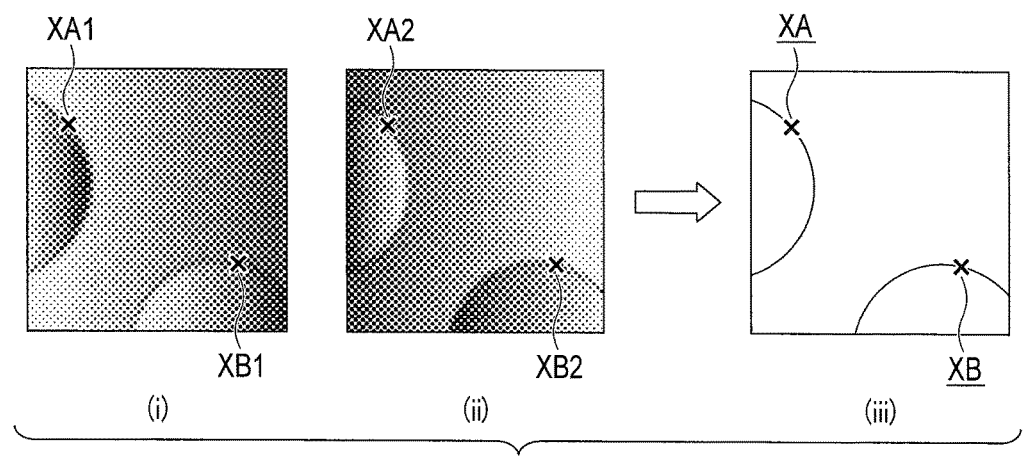
FIG. 2 is a view for explaining identical-point originated pixels when a first image and a second image having set feature points are overlapped.

FIG. 1 shows an entire configuration of an observation system 1 according to a first embodiment of the present invention. FIG. 2(*i*), (*ii*), and (*iii*) are views for explaining identical-point pixels (identical-point originated pixels) when a first image and a second image are overlapped.

The observation system 1 can be implemented separately or incorporated into a device having other functions. This embodiment suggests an example constituted by incorporating constituent parts of the observation system in an inserting section of an endoscope, a light source apparatus, or a video processor. It is to be noted that, when constituent parts of the endoscope have the same functions as those of the constituent parts of the observation system 1, the constituent parts on the endoscope side may also function as those constituent parts of the observation system.

This observation system 1 is roughly constituted of a light source unit (a light source apparatus) 3 which applies illumination light from a distal end of an inserting section 2 of the endoscope, an imager 4 which is a light receiving section and generates an imaging signal, a three-dimensional image generating unit 5 which estimates a surface shape of an observing position (or a later-described identical point) 20a on a specimen 20 from the imaging signal output from the imager 4, and a display (a monitor of the endoscope) 6 which displays image information including a three-dimensional image of the observing position estimated from the surface shape by the three-dimensional image generating section 5.

The light source unit 3 is constituted of irradiation windows 12 and 13 arranged in a distal end surface 2a of the inserting section 2, light converters 14 and 15 arranged in the inserting section 2, and a light emission control section (light emission controller) 7 arranged outside the inserting section 2. The light emission controller 7 may be incorporated into the light source apparatus of the endoscope.

The three-dimensional image generating section 5 is constituted of a controller 21 which controls the entire observation system, an image processer 22, a recorder (an optical information recording section) 23 which records image data (images, information concerning the images, and others) and optical information (light volumes (luminous intensities), address information of captured images, and others), an identical-point originated pixel extracting section (which will be referred to as an extracting circuit) hereinafter) 24, an arithmetic section (arithmetic circuit) 25 which calculates specimen perspective information indicative of an irregular state of a specimen, and a surface shape estimating section 26 which estimates a surface shape of the specimen from the specimen perspective information.

The image processer 22 turns an imaging signal acquired by the imager 4 into image data, and generates various kinds of information including optical information from the image data. The extracting circuit 24 sets feature points 20a (later-described identical points XA and XB) on the specimen to obtain a positional relationship of the specimen in each image in a region which is common to at least two images, and determines pixels (or picture elements) which are these feature points as identical-point originated image pixels (which will be referred to as identical-point pixels hereinafter). Moreover, a pixel of the image sensor which captures the identical-point image pixels on the images will be referred to as an identical-point originated imaging pixel (which will be referred to as an identical-point imaging pixel 4a hereinafter).

The arithmetic circuit 25 calculates specimen perspective information, which represents a relative distance relationship, from light volume information (one of pieces of optical information) of a pixel in an image captured by the imager 4. The surface shape estimating section 26 estimates a surface shape (an irregular shape) of the observing position of the specimen from the specimen perspective information.

As the identical points described here, when a common specimen is shown in images, a given region in these specimen images is arbitrarily determined as the feature point 20a, and feature points which coincide with each other in respective captured images are determined as the identical points. They are referred to as identical-point pixels (XA and XB shown in FIG. 2) in images corresponding to these identical points.

Thus, when positions of the identical points set in images continuously captured by one image sensor have moved in the respective images due to camera shake or movement of the specimen, imaging pixels 4a to image the identical-point pixels are extracted, and address information of these imaging pixels is output as one of pieces of optical information together with image data in association with each other. A signal indicative of light volumes of these identical-point pixels is generated, and specimen perspective information is calculated. It is to be noted that the feature point and the identical point are called points, but they actually suggest a small feature region on a surface of the specimen. Further, the identical-point pixel is not restricted to one pixel, and a pixel group forming a small group or pixels forming a small image region are also included.

In this embodiment, the first irradiation window 12 and the second irradiation window 13 are arranged near a light receiving window 11 arranged near a center of the distal end surface 2a of the inserting section 2. Here, in this embodiment, since an observation window of an observation apparatus which serves as an objective lens of the image sensor also functions as the light receiving window of the endoscope, it will be referred to as the light receiving window in the following description. An illumination window which performs illumination at the time of observation of the observation apparatus also functions as an irradiation window of the endoscope, and hence it will be referred to as the irradiation window in the following description. It is to be noted that the light receiving window 11, the first irradiation window 12, and the third irradiation window 13 are all water-tightly disposed to the distal end surface 2a by using a waterproof member such as a packing member.

In a structural example of this embodiment, the first irradiation window 12 and the second irradiation window 13 are symmetrically arranged apart at substantially the same distance in a diametric direction with the light receiving window 11 at the center on the distal end surface 2a. As a matter of course, the irradiation windows can suffice as long as lights having the same luminous intensity (light volume) are applied to the identical point (e.g., the center of an imaging viewing field) or an observation range of the specimen, distances to the light receiving window 11 on the distal end surface can be adjusted by adjusting the light volumes to be applied, and these windows are not restricted to the symmetrical arrangement shown in FIG. 1.

In this embodiment, the first light converter 14 is arranged to be appressed against or in the vicinity of the first irradiation window 12, the second light converter 15 is arranged to be appressed against or in the vicinity of the second irradiation window 13, and they convert later-described excitation lights (optical signals) into illumination lights respectively. It is to be noted that the irradiation windows in this embodiment have a lens function of performing optical adjustment so that illumination lights 30I and 31I to be applied are uniformly diffused in an imaging viewing field range and a fixed luminous intensity (light volume) is distributed. Additionally, non-illustrated optical members which perform the above-described optical adjustment may be additionally provided between the irradiation windows and the light converters. A fluorescent substance which is a wavelength conversion member is provided at each of distal ends of optical fibers 16 and 17 of the light converters 14 and 15.

The light emission controller 7 includes a light source which applies the excitation lights, and emits the excitation lights to the first light converter 14 and the second light converter 15 through the optical fibers 16 and 17. The first light converter 14 and the second light converter 15 convert the received lights into lights having wavelengths different from those of the received excitation lights, and apply the converted lights to an observation target through the first and second irradiation windows 12 and 13 as the illumination lights 30I and 31I.

In this embodiment, the light emission controller 7 has two blue semiconductor laser light sources which emit lights having the same wavelength mounted therein. These blue semiconductor laser light sources can alternately switch first excitation light to be led to the first light converter 14 and second excitation light to be led to the second light converter 15, and continuously apply these lights.

Further, blue laser lights which are the first and second excitation lights emitted from the blue semiconductor laser light sources are led to the first and second light converters 14 and 15 through the optical fibers 16 and 17 which are, e.g., multimode optical fibers, respectively. The illumination lights subjected to wavelength conversion from the laser lights are applied from the first irradiation window 12 as the first illumination light 30I and from the second irradiation window 13 as the second illumination light 31I. The first illumination light 30I and the second illumination light 31I are applied at different timings. It is to be noted that, when simultaneous irradiation is not performed and these lights are always driven to be alternately applied with a timing difference, one blue semiconductor laser light source and an optical switch can be combined, and two optical fibers are switched to lead the excitation light.

In this embodiment, both the first illumination light 30I and the second illumination light 31I are lights each of which is a combination of blue laser light and white light having a mixed color of yellow fluorescences subjected to the wavelength conversion by these light converters 14 and 15, and they have substantially the same optical characteristics. As a matter of course, they can be adjusted to have substantially the same optical characteristics by controlling an output (an output light volume) of each laser light source with the use of the light emission controller 7. When the optical characteristics (the light volume) are controlled by the light emission controller 7, a non-illustrated optical sensor could be provided, or a signal value to drive the imager 4 could be used to perform feedback control.

The first illumination light 30I emitted from the first light converter 14 is applied to the specimen 20 and reflected and scattered here, and a part of this light turns to reflected light 30R and enters the imager 4. Likewise, the second illumination light 31I emitted from the second light converter 15 is applied to the specimen 20 and reflected and scattered here, and a part of this light turns to reflected light 31R and enters the imager 4.

Since the observation system 1 according to this embodiment is an example applied to the endoscope, this example is a use application of observing a body cavity where external light is rarely present, and light hardly enters the imager 4 except for the reflected lights 30R and 31R of the first illumination light 30I and the second illumination light 31I. Thus, the imager 4 can capture a first image provided by the reflected light 30R of the first illumination light 30I alone and a second image provided by the reflected light 31R of the second illumination light 31I alone.

The imager 4 used in this embodiment is a color image sensor which can perform spectral detection, namely, a spectral detection image sensor in which pixels are arranged in a matrix to form a light receiving surface and, e.g., an RGB primary color filter having a normal Bayer array is provided on this light receiving surface. The image processer 22 extracts first optical information as one of pieces of image information from the first image captured under the first illumination light, likewise extracts second optical information as image information from the second image captured under the second illumination light, and stores them in the recorder 23 in association with the images. The first and second optical information described herein is light volume information of each wavelength region of RGB detected by the imager 4. It is to be noted that, in this embodiment, the first and second optical information is the light volume information of each RGB color pixel in the imager 4 (including address information and others of each pixel), but the present invention is not restricted thereto. Further, information concerning the image sensor and information provided by processing the former information is included.

The extracting circuit 24 compares the first image with the second image, and identifies identical-point pixels which are the identical points (the same feature points) 20a on the specimen 20 respectively. For example, in the captured images, when the same subject is imaged in substantially the same compositions, feature points (the identical points 20a) common to the respective images are set, and these feature points are overlapped, thereby forming one overlapping image. That is, the identical-point pixels are determined in the images captured under the illumination lights applied from different positions, respectively.

In this embodiment, a first identical-point pixel (XA1 in FIG. 2(*i*)) in the first image is a pixel which detects the first optical information at this identical point, and a first identical-point pixel (XA2 in FIG. 2(*ii*)) in the second image is a pixel which detects the second optical information at the common identical point of the same specimen. Furthermore, when J (J: an integer) identical points are set in one image, J identical-point pixels corresponding to this number are present. For example, when three identical points are set in one image, three identical-point pixels corresponding to this plural number are present. Later-described specimen perspective information is calculated from these identical-point pixels, respectively.

The extracting circuit 24 compares the first image with the second image, and identifies the identical points on the images. Various techniques can be applied to identification of the identical points.

For example, when a position of the specimen differs in two images captured by one image sensor, image processing of extracting common feature points (identical points) of the specimen in the respective images is executed. As shown in FIG. 2(*iii*) which will be described later, when a positional relationship between the two images is specified so that these feature points overlap, the identical points in the two images can be identified, and the identical-point pixel of the corresponding imager 4 can be selected.

As another example, when emission timings for the first illumination light and the second illumination light are switched at a timing sufficiently earlier than a moving speed of the distal end surface 2a of the inserting section 2, imaging is continuously performed in a substantially immobile state. Further, since the distal end surface 2a is moved while performing observation, its moving speed is generally slow. Thus, as regards identical points on the subjects in the captured images, a position of a pixel in the first image substantially coincides with a position of a pixel in the second image.

The identical-point pixel (the identical-point originated pixel) when the first image overlaps the second image will now be described with reference to FIG. 2(*i*), (*ii*), and (*iii*).

It is possible to adopt an algorithm of combining these images, determining pixels of the same specimen in images as tentative identical points, and finely adjusting a position by image processing or the like. The first image and the second image continuously captured in a short time are two images captured when the image sensor is placed at substantially the same positions to the specimen. Thus, as shown in FIGS. 2 (*i*) and 2 (*ii*), at least two sets of feature points (first feature points: XA1 and XB1) (second feature points: XA2 and XB2) are extracted as identical points, and the first image and the second image are arranged so that these two sets of feature points (XA1 and XA2, XB1 and XB2) overlap each other.

As to this overlapping arrangement, since two overlapping images show the same specimen in substantially the same compositions, these feature points also accordingly overlap at two points (XA and XB) as shown in FIG. 2(*iii*). Thus, in an overlapping image, all the feature points can be set as the identical points in the two images, and pixels which image these identical points serve as the identical-point pixels. Here, pixels which image the feature points XA1, XB1, XA2, and XB2 are determined as a first image first identical-point pixel (XA1), a first image second identical-point pixel (XB1), a second image first identical-point pixel (XB2), and a second image second identical-point pixel (XB2). Moreover, when J (J: an integer) identical points are present, a first image J-th identical-point originated pixel and a second image J-th identical-point originated pixel are determined.

Then, the arithmetic circuit 25 compares and calculates the first optical information of the first image and the second optical information of the second image output from the extracting circuit 24, and extracts the identical points (or arbitrary measurement regions) of the specimen as the feature points. In this embodiment, extraction is performed on the basis of the light volume information which is one of pieces of optical information of the identical-point pixels in the first and second images. As the extracting method, it is possible to adopt a feature point detecting method which is used in a publicly known image pasting technique. As the detection method, there is, e.g., one of pattern detection techniques by which a pixel group including a feature pixel and its surrounding pixels is set on one image, a pattern based on an image signal value or a light volume value is generated, and a pixel group coinciding with this pattern is searched in the other image.

Figure 3:
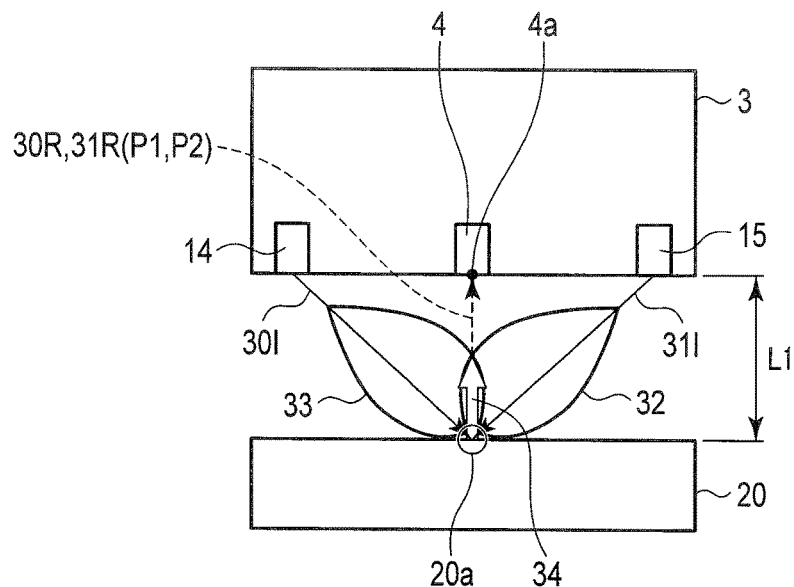
FIG. 3 is a view showing a conceptual arrangement example of acquiring specimen perspective information from illumination lights in a state where the observation system is close to the specimen at a distance L1.
Figure 4:
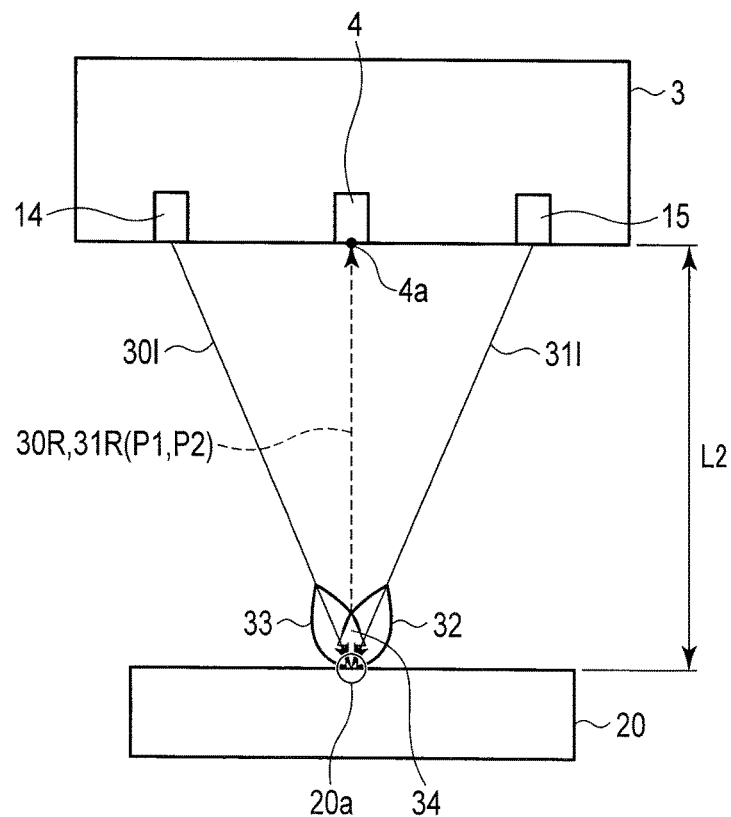
FIG. 4 is a view showing a conceptual arrangement example of acquiring the specimen perspective information from the illumination lights in a state where the observation system is away from the specimen at a distance L2.

FIG. 3 is a view showing a conceptual arrangement example of acquiring specimen perspective information from the illumination lights in a state where the observation system 1 is close to the specimen at a distance L1. FIG. 4 is a view showing a conceptual arrangement example of acquiring specimen perspective information from the illumination lights in a state where the observation system 1 is apart from the specimen 20 at a distance L2. FIG. 5 is a view conceptually showing heights from flat surfaces provided by reflected light volumes when the first illumination light and the second illumination light are applied to the specimen.

In FIG. 3 and FIG. 4, one light beam in diffusion lights of the respective white illumination lights is indicated by a solid line and a dotted line. Additionally, light distributions (light distribution information) each having a drop-like shape parallel to optical axes of the reflected lights 30R and 31R are shown on an axisymmetric opposite side of incidence angles of the respective illumination lights 30I and 31I. This light distribution information represents a relationship between an irradiating direction of the light source and light intensity, and is recorded in the recorder 23 as one of pieces of information concerning images.

The arithmetic circuit 25 extracts a light receiving amount P1 (the reflected light 30R) which is light volume information in the first image and a light receiving amount P2 (the reflected light 31R) which is light volume information in the second image to the identical-point pixels associated with the extracted identical points 20a, and calculates light volume ratio information P1/P2 which is a rate of the extracted information. This light volume ratio information P1/P2 is a ratio of a light volume of the light emitted through the first irradiation window 12 which is reflected and scattered at the identical points 20a and enters the imager 4 and a light volume of the light emitted through the second irradiation window 13 which is reflected at the identical points and enters the image sensor.

Then, on the basis of the light volume ratio information P1/P2, grouping is performed in accordance with each identical-point pixel. For example, the pixels are divided into three groups, i.e., P1/P2>1 . . . a first group, P1/P2≈1 . . . a second group (an equal light volume ratio), and P1/P2<1 . . . a third group.

Here, when the ratio of the light volume ratio information P1/P2 is "1" (an absolute value) or "substantially 1" of the second group, i.e., when the two identical-point pixels are identical-point light volume pixels having an equal light volume ratio, as shown in FIG. 5, the identical points on the surface of the specimen face the distal end surface (the flat surface) of the inserting section 2, in which the irradiation windows are arranged, in parallel, and it can be estimated that the identical points on the surface are provided on a flat surface portion. As described above, the light volume ratio enables estimating whether the surface is flat, but it does not represent magnitudes of the light volumes, and hence perspective about a distance cannot be estimated. Heights of the flat portion, i.e., distances from the imager 4 to the specimen can be calculated from the light volumes detected by the imager 4 with the use of the above-described triangulation method or the like.

The arithmetic circuit 25 compares magnitudes of the identical points 20a included in the second group of the equal light volume ratio information P1/P2≈1 on the basis of the absolute value of the light volume of P1 (≈P2). A magnitude of the light volume of P1 (≈P2) relates to the perspective of the distance between the imager 4 and the identical point 20a on the specimen 20. That is, when P1 (≈P2) is compared in relation to magnitudes, it can be understood that an identical point d1 having a larger light volume is closer to the imager 4 than an identical point d2 having a smaller light volume and it has a shorter distance L.

Thus, the arithmetic circuit 25 calculates the specimen perspective information which is a relative distance relation from the imager 4 to the specimen 20 on the basis of the light volumes detected by the imager 4. Further, the surface shape estimating section 26 estimates an irregular state of an observing position on the specimen from the specimen perspective information and images associated with identical points read from the recorder 23, and forms a three-dimensional image from the images on the basis of perspective (irregularity) emphasis. It is to be noted that data provided by previously acquiring light distribution information when lights emitted from the illumination lights strikes and reflected on a substance (e.g., a tissue of a surface layer) and stored in the recorder is used. This light distribution information is provided by detecting data of each measurable substance (including blood vessels and others) and storing them in advance. If a substance stored in the storage data is inclined, a light distribution of reflected lights from the illumination lights is also inclined, an intensity of a light volume of a component received by the image sensor changes, and hence an inclination of this region (the substance) can be recognized, which enables correcting irregularities on the surface on the basis of a relationship between pixels adjacent to each other.

Here, when flat surface portions alone are estimated, in FIG. 5, on the basis of a difference between light volumes detected by the imager 4, it is estimated that a flat surface portion d1 is higher than a flat surface portion d2 and is present on a top portion side, an irregular state that the flat surface portion d2 is present on a bottom portion side is provided between the flat surface portion and the flat surface portion, e.g., between the flat surface portion d1 and the flat surface portion d2, and these flat surface portions are connected through an inclined portion.

The inclined portion between the flat surface portion and the flat surface portion will now be described with reference to FIG. 6 and FIG. 7.

FIG. 6 is a view showing a relationship between light volumes of two reflected lights when the distal end surface 2a of the inserting section 2 faces the surface of the specimen 20 at a slant. FIG. 7 is a view conceptually showing inclinations of the surface of the specimen on the basis of a ratio of reflected light volumes of the first illumination light and the second illumination light.

A description will now be given as to a case where P1/P2> in the first group and P1/P2<1 in the third group.

As shown in FIG. 6, when the distal end surface 2a faces the surface of the specimen 20 at a slant, a ratio of the reflected and scattered light volumes on the specimen 20 changes depending upon incidence directions of the illumination lights to an observation axis which is an imaging viewing field direction (an arrow 34 in FIG. 6) of the imager 4. The observation axis is an observing direction of the image sensor, which is generally a perpendicular line to the flat surface at the distal end. How much the observing surface of the specimen is inclined from this observing axis is represented as an observation axis inclination angle.

That is, when the specimen has the observation axis inclination angle to the light receiving surface of the image sensor, the reflected light volume of the first illumination light has a smaller reflection angle than that of the reflected light volume of the second illumination light. When this reflection angle is small, the reflected light 30R of the first illumination light 30I enters the light receiving surface of the imager 4 while a portion of the light distribution with a high light volume is close to the observation axis 34. Contrarily, when this reflection angle is large, the reflected light 31R of the second illumination light 31I enters the imager 4 while a portion of the light distribution with a high light volume is away from the observation axis 34. As a result, since the inclination is present, a light volume 32 of the first reflected light 30R received by the imager 4 is larger than a light volume 33 of the second reflected light 33. That is, P1 is different from P2, and P1/P2 becomes other than 1.

In FIG. 6, since the first reflected light volume 30R is larger than the second reflected light volume 31R, it can be estimated that the inclination of the specimen 20 is high on the right side (the opposite side of a light source position having the high reflected light volume).

That is, as shown in FIG. 7, when P1/P2<1 of the third group is achieved, an inclined state of an inclined portion d5 is provided. Contrarily, when P1/P2 in P1/P2>1 of the first group is larger than 1, like an inclined portion d4, an inclined state opposite to that of the inclined portion d5 is provided. An inclination angle varies depending on a difference in height of the flat surface portions connected to each other, e.g., the flat surface portion d1 and the flat surface portion 3 to the flat surface portion d2, and this inclination angle can be estimated from a difference in light volume of P1 and P2.

In this embodiment, the arithmetic circuit 25 extracts the second group including pixels having the light volume ratio information P1/P2≈1, i.e., P1 and P2 which are substantially equal to each other (pixels having the identical light volume) as the identical points 20a on the flat surface portion of the specimen. Furthermore, it estimates each flat surface portion of the specimen from the first specimen perspective information obtained from the pixels of the second group. Moreover, as shown in FIG. 7, when long-distance information is acquired at a position where the equal light volume ratio pixels have a ratio which is different from 1/1, e.g., 1/2, detailed far-distance information can be acquired by adding the position of 1/2 to the position of 1/1.

Then, the arithmetic circuit 25 sets the identical points 20a on all or a part of the surface of the specimen to the pixels excluding the pixels of the second group. Second specimen perspective information which is indicative of each relative distance relationship is calculated by using light volumes of the identical-point pixels at the imaged identical points 20a. Since a surface estimated from this second specimen perspective information does not include the pixels of the second group, i.e., the flat surface portions of the specimen, it can be understood that the surface is an inclined portion which is inclined in any direction.

Thus, the flat surface portion and the flat surface portion of the second group are smoothly connected with each other by the inclined portion calculated from the second specimen perspective information, thereby estimating the irregular state of the specimen as shown in FIG. 7. Additionally, the surface shape estimating section 26 reads out an image stored in the recorder 23, reflects the calculated specimen perspective information to all or a part of the image, emphasizes the perspective (an irregular shape), forms a three-dimensional image of the image which is a target of stereoscope image creation, and outputs it to the display 6.

Figure 8A:
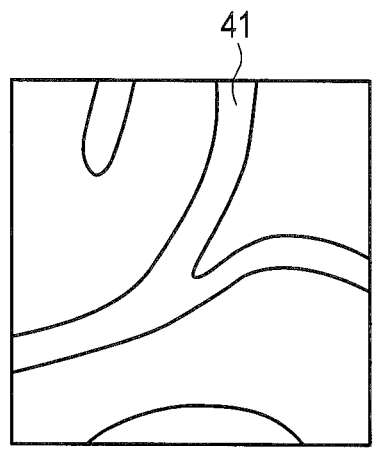
FIG. 8A is an image view showing an observation screen of a two-dimensional image of the specimen imaged by the observation system before perspective emphasis.
Figure 8B:
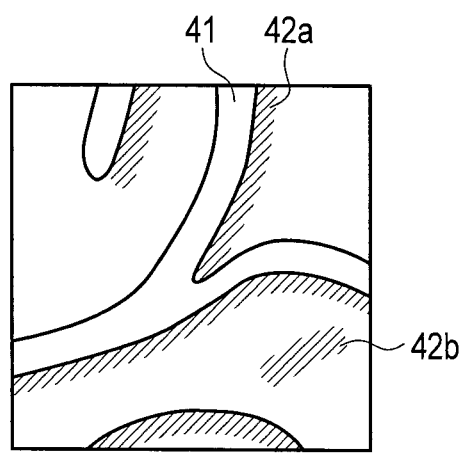
FIG. 8B is an image view showing an observation screen of a three-dimensional image of the specimen imaged by the observation system according to this embodiment after the perspective emphasis.

FIG. 8(i) is an image view showing an observation screen of a two-dimensional image before performing the perspective emphasis to the specimen imaged by the endoscope having the observation system mounted therein, and FIG. 8(ii) is an image view showing an observation screen of the three-dimensional image after performing the perspective emphasis to the specimen imaged by the endoscope in which the observation system 1 having the three-dimensional image generating section 5 according to this embodiment is mounted.

In FIGS. 8(i) and 8(ii), for example, when the perspective (irregularity) emphasis using a stereoscopic image estimated from the specimen perspective information is performed to a region 41 which is linearly raised like rugae of intestines or the like, an observing region or a treatment target region can be stereoscopically displayed. As shown in FIG. 8(ii), a region 42a having emphasized irregularities or a region 42b before the irregularity emphasis which cannot be confirmed in FIG. 8(i) can be easily seen. Such three-dimensional image display enables giving a sense of distance or a stereoscopic effect between regions to an operator or an observer, reducing a burden imposed when performing a grip operation or a treatment operation of a treatment target region, and aiding a diagnosis or a judgment at the time of observation.

Further, in this embodiment, since the primary color image sensor having the RGB Bayer array is used, as to the first and second image light receiving amounts P1 and P2, information of P1-R, P1-G, P1-B, P2-R, P2-G, and P2B can be detected as dispersed color information of each color of RGB. Information obtained by adding these pieces of information in accordance with P1 or P2 may be used as light volume information. Further, information of a color pixel having a high spectral reflectance (spectral reflectance information) of the specimen may be used. In the case of a medical endoscope which uses a specimen as a body tissue, the body tissue has a high spectral reflectance of red, and P1-R and P2-R have values higher than those in the light volume information of the other colors. Thus, using the light volume information of red alone enables acquiring specimen perspective information having a higher accuracy.

Further, a measurement value obtained by actual measurement in advance or a numeral value disclosed in a literature of the like is acquired as the spectral reflectance information to a substance such as an inner blood vessel or a tissue of a surface layer which is a measurement target, and stored in the recorder 23. The spectral reflectance information of a region (or the substance) obtained by the actual measurement can be compared with the spectral reflectance information stored in the recorder 23 to estimate whether the measurement target is the surface or the inside and correct the perspective information.

Figure 9:
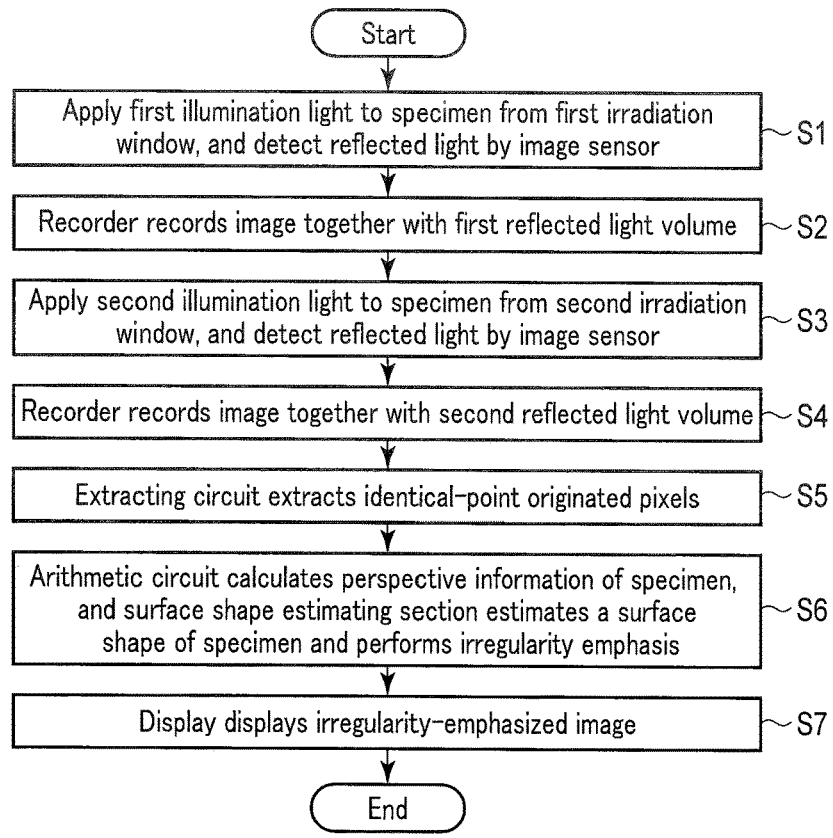
FIG. 9 is a flowchart for explaining display of the perspective (irregularity) emphasis.
Figure 10:
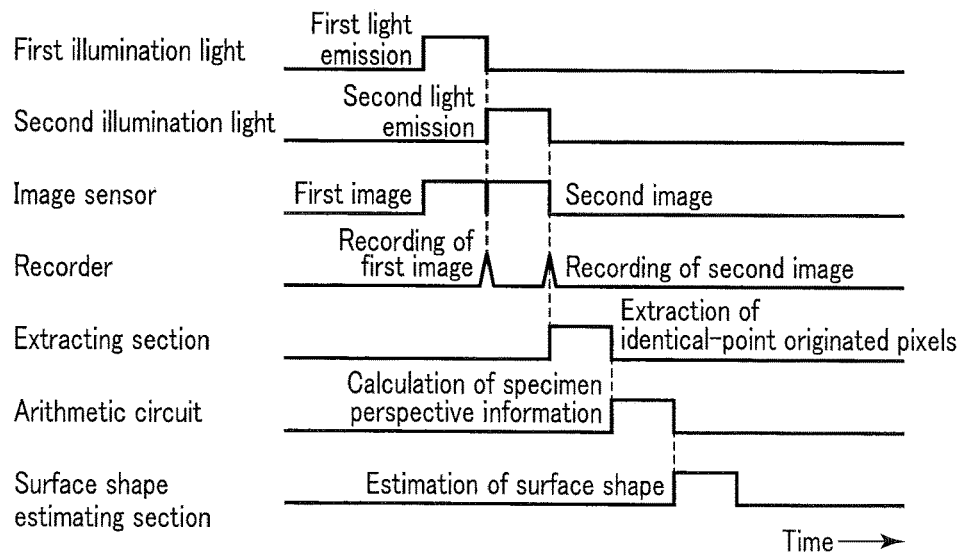
FIG. 10 is a timing chart for explaining the display of the perspective (irregularity) emphasis.

Display of the perspective (irregularity) emphasis will now be described with reference to a flowchart shown in FIG. 9 and a timing chart shown in FIG. 10.

First, the first light converter and the second light converter are controlled to have different irradiation timings by the light emission controller 7. At first, the light emission controller 7 applies the first illumination light 30I to an observing position on the specimen 20, and the imager 4 receives the reflected light 30R from the specimen 20 and outputs a first imaging signal to the image processor 22 (a step S1). The image processor 22 calculates a first reflected light volume provided by the received reflected light from the first imaging signal, and records it in the recorder 23 together with image data (a step S2).

Subsequently, the light emission controller 7 applies the second illumination light 31I to the observing position on the specimen 20, and the imager 4 receives the reflected light 31R from the specimen 20 and outputs a second imaging signal to the image processor 22 (a step S3). The image processor 22 calculates a second reflected light volume provided by the received reflected light from the second imaging signal, and records it in the recorder 23 together with image data (a step S4).

Then, the extracting circuit 24 compares pixels in an image having the first reflected light volume read from the recorder 23 with pixels in an image having the second reflected light volume, and extracts identical-point pixels within the observing position a step S5).

The arithmetic circuit 25 calculates the specimen perspective information of the observing position (a flat surface portion) where P1/P2≈1 as a ratio of the light volume information of the extracted identical-point pixels is achieved. Furthermore, the above-described inclined portion may be subsequently calculated. Moreover, the surface shape estimating section 26 estimates a surface shape of the observing position of the specimen from the calculated specimen perspective information, and performs image processing which is the irregularity emphasis to the image read from the recorder 23 (a step S6). The display 6 displays an image of the observing position subjected to the irregularity emphasis (a step S7).

According to this embodiment, as described above, the illumination lights are applied to the specimen at different light emission timings from the light sources provided at positions equally apart from one image sensor, pieces of pixel information of images captured with respective reflected light volumes are compared with each other to identify at least one of identical regions of the specimen, and the perspective information of the specimen is acquired based on a magnitude of an absolute value of a reflected light volume ratio which corresponds to substantially equal ratios of the reflected lights (the first reflected light volume/the second reflected light volume) of the respective light sources at the respective regions. Even if surfaces of the regions are wet with mucus and diffused reflection occurs, the regions where reflection spectrums from the two or more different light sources are the same can be recognized as the same flat surface. Additionally, a relationship in inclination between regions having substantially the same or different light volume ratios (the first reflected light volume/the second reflected light volume) is measured, and the inclinations are identified based on magnitudes of the light volume ratios, thereby easily estimating a perspective (irregular) state of the specimen.

Further, as shown in FIG. 7, when positions of the detected flat surface portion and inclined portion are recognized and regions adjacent to each other are connected while considering an inclining direction, the perspective (irregularity) information of each region can be estimated, and the specimen can be three-dimensionally displayed in more detail.

According to this embodiment, dispersion of dyes is not required for a scene which requires a "dye method" of dispersing various kinds of dyes and observing its reaction in conventional examples, and the perspective (irregularity) emphasis can be easily and assuredly realized. Since dyes are not dispersed, normal observation of an original tissue can be continued, and a use state or a configuration of an existing endoscope does not have to be greatly changed, and hence the reliability and costs are excellent.

Furthermore, a treatment burden of dispersion of the dyes imposed on an operator can be alleviated, a sense of distance can be easily obtained to a treatment region since a stereoscopic image of an observation target is created, a treatment time can be shortened, and a burden on a patient can be reduced.

It is to be noted that the identical-point pixel (the identical-point originated pixel) is defined as one pixel of the image sensor, but it is not restricted to one pixel. For example, imaging pixels (a pixel group) of the image sensor can be collected up, and specimen perspective information can be obtained by using light volume information detected by the pixel group. For example, when 3×3 pixels are determined as one pixel group, a sum of pieces of light volume information detected by each pixel constituting the pixel group is defined as the light volume information detected by the pixel group. Consequently, as subsequent techniques, the specimen perspective information can be calculated by performing the same processing as that of the foregoing embodiment, and a surface shape of the specimen can be estimated.

Moreover, when the pixel group has pixels which have different detectable spectral regions, determining a sum of individual pixels having the same spectral region alone as the light volume information detected by the pixel group enables calculating and estimating the specimen perspective information or a surface shape of the specimen.

Additionally, as to the positional relationship between the first irradiation window, the second irradiation window, and the image sensor, the description has been given as to the embodiment where the first irradiation window and the second irradiation window are symmetrically arranged at an equal interval with the image sensor at the center, an image may be acquired by correcting a light volume ratio applied from the first irradiation window and the second irradiation window or a distance relationship between the first irradiation window, the second irradiation window, and the image sensor even if the image sensor is shifted from an axis connecting the first irradiation window with the second irradiation window.

Further, as a first modification, when the arithmetic circuit 25 calculates the specimen perspective information indicative of an irregular shape of the specimen 20, at the time of detecting the first reflected light volume and the second reflected light volume by using the imager 4, an inclination of the surface shape of the specimen 20 to the flat light receiving surface of the imager 4 is determined as inclination information obtained by sequentially combining light volume values output from the adjacent pixels, and the image can be subjected to image processing to turn to a perspective (irregularity) emphasized image based on the inclination information, thereby creating and displaying a three-dimensional image.

As a second modification, it is possible to identify, from color information such as an RGB ratio of each pixel, a type of the specimen 20 having the same color information and improve an accuracy of information of a region. Further, as a configuration which is not restricted to the RGB light source, for example, with the use of the imager 4 having no color filter provided thereto and a field sequential system of alternately applying R light, G light, and B light from two irradiation window, a combination of six images obtained by the imager 4 (a first R light image, a second R light image, a first G light image, a second G light image, a first B light image, and a second B light image) is used, and a type of the specimen 20 can be identified from color information of these images, and accuracy of information of a region can be improved.

A third modification will now be described. In the above-described first embodiment, pixels having the same light volume which can realize a light volume ratio P1/P2≈1 are used as an observing position, but pixels having different light volumes which realize P1/P2≈α (α is a predetermined positive number) can be used. In the above-described first embodiment, although a surface orthogonal to the observation axis is determined as the observing position, a surface having an arbitrary inclination angle to the observation axis is extracted as the observing position in this modification. Even if an observing surface of the specimen 20 is inclined to the observation axis by this setting of the light volume ratio and identical-point pixels which realize P1/P2≈1 are rarely obtained, a sufficient number of identical-point pixels can be obtained. It is desirable to set a value of this α on the basis of the inclination angle of the surface of the specimen to the observation axis.

Second Embodiment

An observation system according to a second embodiment has the same configuration as that of the above-described first embodiment, and like reference numerals denote like constituent parts to omit a description thereof.

FIG. 11 is a view showing a conceptual arrangement example of acquiring specimen perspective information from illumination lights in a state where an observation system 1 according to the second embodiment is close to a specimen 20 at a distance L/2. FIG. 12 is a view showing a conceptual arrangement view of acquiring the specimen perspective information from the illumination lights in a state where the observation system is apart from the specimen 20 at a distance L.

In the foregoing embodiment, the specimen perspective information is calculated to pixels having the same light volume (identical-point originated pixels) which realize P1/P2≈1 in accordance with a magnitude relation of light receiving amounts.

When a light source unit 3 is close to the specimen 20, a reflected light volume P1 increases in proportion to a distance between them. For example, FIG. 11 shows an example where a distance between the imager 4 and the specimen 20 is L/2. Contrarily, when the light source unit 3 is distant from the specimen 20, a reflected light volume P2 decreases in proportion to a distance between them. FIG. 12 shows an example where a distance between the imager 4 and the specimen 20 is, e.g., L.

At this time, assuming that a scattering mode when the imager 4 and the specimen 20 scatter the illumination lights is isotropic scattering, a light receiving amount received by each identical light volume pixel decreases in inverse proportion to a square of a distance between the imager 4 and an identical point 20a on the specimen 20. As shown in FIG. 13, the distance can be calculated as a value which is in proportion to an inverse number of a square root of the light receiving amount received by the identical light volume pixel. For example, when the distance L is doubled, a measurable light volume is ¼-fold. When the light volume is taken as a plane area, a light volume which can be received by the imager 4 having a finite size has an inverse relationship to the distance. Further, even if the specimen 20 does not perform the isotropic scattering, rough relative distance information can be obtained by the above-described technique.

As described above, according to this embodiment, in addition to functions and effects of the foregoing first embodiment, a surface shape or an irregularity emphasized image with a higher accuracy can be obtained.

Third Embodiment

An observation system according to a third embodiment will now be described with reference to FIG. 14 and FIG. 15. Although the structural example where the two irradiation windows are symmetrically arranged at substantially equal intervals in the diametric direction with the light receiving window at the center has been described in each of the foregoing first and second embodiments, the arrangement of these windows is not restricted thereto. An observation system according to the third embodiment is an observation system in which a light source unit has three or more irradiation windows. Constituent parts other than the light source unit in this embodiment are equal to the structures in the first embodiment, and like reference numerals denote like constituent parts to omit a description thereof.

The light source unit 3 according to this embodiment shown in FIG. 14 corresponds to a structural example where three irradiation windows 13, 14, and 51 are arranged at an equal distance with one light receiving window 11 at the center in a distal end surface 2a of an inserting section 2. Appropriate two irradiation windows are selected from these three irradiation windows 13, 14, and 51, and the same three-dimensional image creation processing as that in the foregoing first embodiment is carried out.

Figure 15:
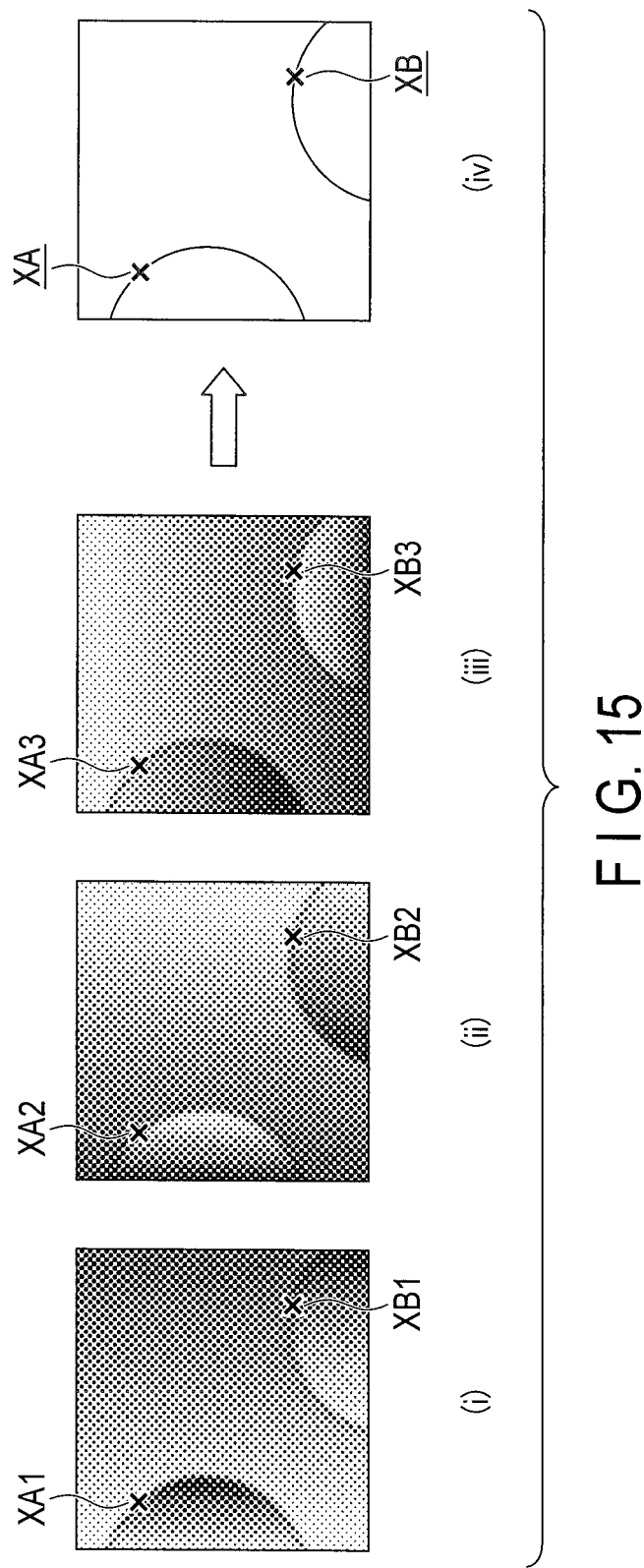
FIG. 15 is a conceptual view for explaining acquisition of specimen perspective information from illumination lights applied through three or more irradiation windows.

Furthermore, as shown in FIG. 15(*i*), (*ii*), and (*iii*), respective pieces of light volume information of illumination lights emitted from three or more irradiation windows can be used to obtain specimen perspective information in FIG. 15(*iv*) with the use of the above-described technique.

For example, when the three irradiation windows 13, 14, and 51 are arranged, defining pixels as identical light volume pixels so that P1=P2=P3 can be achieved enables extracting, as observing positions, pixels parallel to a plane substantially vertical to an observation axis defined from a positional relationship of the three irradiation windows 13, 14, and 51 and the imager 4.

Moreover, in the case of an inclination to the observation axis, pixels can be extracted as observing positions so that (P1:P2:P3≈1:β:γ) can be always achieved.

Consequently, as compared with the example using the two irradiation windows alone, more accurate specimen perspective information can be obtained. Additionally, since the arrangement of the light source to the image sensor two-dimensionally spreads, the configuration using the two irradiation windows alone enables highly accurately detecting relative distance information of an array direction of the light sources, but the accuracy is relatively lowered to a direction orthogonal to this direction, whereas the configuration having three or more irradiation windows enables highly accurately detecting the relative distance information in any direction.

As described above, according to this embodiment, when appropriate two irradiation windows are selected from these three irradiation windows 13, 14, and 51, the same effects as those of the foregoing first embodiment can be provided. Further, since the third irradiation window 51 is added, the number of images captured under the illumination light emitted from a different direction (y) is increased, more pieces of specimen perspective information can be acquired, and a further detailed three-dimensional image can be estimated.

A modification of the third embodiment will now be described.

This modification is a configuration in which the observation system has four or more irradiation windows arranged therein.

A structural example can be realized by the configurations shown in FIG. 1 and FIG. 4 except for the configuration where the illumination windows are arranged to apply illumination lights.

For example, an image of the specimen 20 is captured through one light receiving window 11 having the imager 4 arranged therein. The light receiving window 11 is arranged at the center, and irradiation windows are arranged near this window. The light emission controller 7 selectively sequentially applies illumination lights having the same optical characteristics generated by the light source apparatus to the specimen 20 through the irradiation windows. Under the selectively and sequentially applied illumination lights, the imager 4 takes in images captured in accordance with each illumination light, and outputs them as an imaging signal to the image processer 22. The image processer 22 generates optical information included in each image, and records optical information in the recorder 23 in association with the image.

The identical originated pixel extracting circuit 24 reads images from the recorder 23 under control of the controller 21, and sequentially sets the same feature points (XA or the like) on the specimen 20 as identical points. Specifically, it sets at least two tentative feature points in one image, and confirms whether the tentative feature points are present in all the other images. If the tentative feature points are present in all the images, these tentative feature points are set as identical points. Further, when the tentative feature points are not present in all the images, tentative feature lines are again set, and their presence is confirmed. The feature points present in all the images are set as identical points.

Then, one image is determined as a reference image, and at least two identical points are determined as reference identical points. Each of the images is moved so that the two identical points are placed at the reference identical points, thereby performing image overlapping processing. Pixels which have imaged these identical points are extracted as identical-point originated pixels, and they are output to the arithmetic circuit 25 together with values of light volumes output from these pixels.

The arithmetic circuit 25 calculates specimen perspective information in which values of light volumes included in optical information output from the identical-point capturing pixels are determined as relative distances from the imager 4, and outputs it to the surface shape estimating section 26. It is to be noted that the values of the light volumes of the identical-point pixels in the captured images may be output to the arithmetic circuit 25 from the recorder 23.

The surface shape estimating section 26 compares the optical information output from the identical-point originated pixels, which have imaged the identical points common to the images, between the images forming a pair on the basis of the specimen perspective information. An identical point having a comparison result which is substantially 1 is determined as a flat surface portion, an identical point having a comparison result which exceeds substantially 1 is determined as a first inclined portion, and an identical point having a comparison result which is less than substantially 1 is determined as a second inclined portion. The flat surface portion and the first and second inclined portions are associated with the calculated relative distances on the basis of these determinations, and a surface shape of the specimen is estimated. The display 6 displays a stereoscopic image based on the surface shape estimated by the surface shape estimating section.

It is to be noted that another processing method of setting identical points to images captured under illuminations will now be described. The processing to set the identical points is performed to all the images, and hence a case requiring a processing time can be presumed depending on the number of illumination windows. Thus, a further modification of the identical-point setting will now be described.

First, as described above, images of a specimen captured under illumination lights continuously and sequentially applied from the illumination windows are recorded in the recorder 23.

Then, of these images, two images (images A and B) captured under the illumination of two arbitrary illumination windows arranged on both sides of the light receiving window are determined as a first pair of images. A second pair of illumination windows arranged on a straight line in an arbitrary direction crossing a direction of a straight line connecting positions of these illumination windows are selected, and two images (images C and D) captured under the illumination of these illumination windows are determined as a second pair of images.

The same feature point (XA or the like) on the specimen 20 captured in each of these pair of images respectively is determined as an identical point, and the identical points are set, pixels which have imaged these identical points are extracted as identical-point originated pixels, and they are output to the arithmetic unit 25 together with values of light volumes output from these pixels.

The subsequent calculation of the specimen perspective information by the arithmetic circuit 25 and estimation of the surface shape of specimen by the surface shape estimating section 26 are the same as those of the foregoing modification.

Thus, if the observation system has the configuration in which three or more irradiation windows are arranged, combining this system with the first and second embodiments enables acquiring more accurate specimen perspective information and the various kinds of information obtained therefrom while maintaining advantageous effects. It is to be noted that the foregoing embodiments and modifications are just examples, and they can be modified in many ways without departing from the gist of the invention.

According to the present invention, it is possible to provide an observation system which can acquire perspective information suggesting an irregular state of a surface of a specimen from captured images captured under illumination lights sequentially applied at continuous timings through the irradiation windows at different positions aligned in one imaging optical system, and can display a three-dimensional observation image based on the perspective information.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An observation system comprising:
   a light source apparatus comprising:
      a first irradiation window through which first illumination light is applied,
      a second irradiation window through which second illumination light is applied;
      an image sensor which captures images of a specimen irradiated with the first and second illumination lights, and
      a light emission controller which emits the first illumination light and the second illumination light at different timings,
      wherein the first and second illumination lights have substantially equal optical characteristics, and
      the image sensor is configured to acquire a first image which is an image of the specimen provided by the first illumination light alone and to acquire a second image which is an image of the specimen provided by the second illumination light alone, wherein the first image includes first optical information and the second image includes second optical information, respectively,
   an optical information recorder which records the first optical information and the second optical information; and
   a controller comprising hardware, the controller being configured to:
      compare the first image with the second image, associate a first image identical-point originated pixel as an identical-point originated pixel in the first image and a second image identical-point originated pixel as an identical-point originated pixel in the second image, which are originated from an identical point at three or more positions on the specimen, with each other, and extract a first identical point and a second identical point as identical points on the specimen,
      compare first optical information which is first light volume information of the specimen based on the first illumination light, detected from a first image first identical-point originated pixel at the first identical point at the three or more positions with second optical information which is second light volume information of the specimen based on the second illumination light, detected from a second image first identical-point originated pixel,
      compare first optical information which is first light volume information of the specimen based on the first illumination light, detected from a first image second identical-point originated image at the second identical point at the three or more positions with second optical information which is second light volume information of the specimen based on the second illumination light, detected from a second image second identical-point originated pixel, and
      in all of the first identical point and the second identical point on the specimen, calculate light volume ratio information which is a ratio of the first light volume information of the first image J-th identical-point originated pixels and the second light volume information of the second image J-th identical-point originated pixels, where J is an integer which is 1 or more, and, when pixels, the light volume ratio information of which are substantially equal, are determined as equal light volume ratio pixels, and when the first and second images include a plurality of equal light volume ratio pixels, calculate, on the basis of magnitudes of the light volume information of the equal light volume ratio pixels, specimen perspective information which is a relative distance relationship from the image sensor;
      estimate a surface shape of the specimen from the specimen perspective information; and
      display a stereoscopic image to which the estimated surface shape is reflected.

2. The system according to claim 1,
   wherein, of the equal light volume ratio pixels, a pixel having the first light volume information and the second light volume information at the J-th identical point which are equal to each other is assumed to be an identical-point light volume pixel, and
   the controller calculates distance information between the specimen and the image sensor as the specimen perspective information on the basis of a magnitude of an absolute value of a light volume of the identical-point light volume pixel.

3. The system according to claim 2, wherein the controller calculates the distance information as a value which is in proportion to an inverse number of a square root of an absolute value of a received light volume of either the equal light volume ration pixel or the identical light volume pixel.

4. The system according to claim 1, wherein the controller calculates an observation axis inclination angle to an observation axis, which is defined by the image sensor, the first irradiation window, and the second irradiation window, to the identical point on the specimen on the basis of the light volume ratio information.

5. The system according to claim 4, wherein the controller calculates the observation axis inclination angles of continuous pixels having the different pieces of light volume ratio information respectively, smoothly connects the pixels having different observation axis inclination angles on the basis of a continuous positional relationship in an image, and calculates a surface shape of the specimen.

6. The system according to claim 1, wherein the optical information recorder has light distribution information which is a relationship between an irradiating direction and light intensity of the light source, and the controller corrects the specimen perspective information on the basis of the light distribution information.

7. The system according to claim 1,
   wherein the optical information recorder has spectral reflectance information of the specimen, and
   the controller corrects the specimen perspective information on the basis of the spectral reflectance information.

8. The system according to claim 1,
   wherein the image sensor is a spectral detection image sensor which is configured to perform spectral detection to the first and second illumination lights on the basis of wavelengths, and
   the controller calculates the specimen perspective information on the basis of predetermined wavelength band light volume information which is light volume information in a predetermined wavelength band in the first and second optical information received by the image sensor.

9. The system according to claim 8, wherein the predetermined wavelength band is a region where a spectral reflectance of the specimen is high.

10. The system according to claim 1, wherein the first image J-th identical-point originated pixels forms a pixel group constituted of pixels, the first image J-th identical-point originated pixels and the second image J-th identical-point originated pixels have the same number of pixels and the same pixel arrangement, and controller calculated the first and second optical information is calculated on the basis of a pixel configuration of the pixel group.

11. The system according to claim 10, wherein the first and second optical information is a sum of pieces of optical information of each pixel constituting the pixel group.

12. The system according to claim 10, wherein the image sensor is a spectral detection image sensor configured to perform spectral detection on the basis of wavelengths of the first and second illumination lights, and the pixel group includes pixels having different detectable spectral regions, and the first and second optical information is obtained as a sum of respective pixels having the equal spectral region.

13. The system according to claim 1, wherein the light source apparatus comprises three or more irradiation windows, selects two from the irradiation windows to apply illumination lights, and calculates the specimen perspective information from captured images.

14. An observation system comprising:
a light source apparatus comprising:
   a first irradiation window through which first illumination light is applied,
   a second irradiation window through which second illumination light is applied,
   a third irradiation window through which third illumination light is applied; and
an image sensor which captures images of a specimen irradiated with the first, second, and third illumination lights,
a light emission controller which emits the first illumination light, the second illumination light, and the third illumination light at different timings,
wherein the first, second, and third illumination lights have substantially equal optical characteristics, and
the image sensor is configured to acquire a first image which is an image of the specimen provided by the first illumination light alone, to acquire a second image which is an image of the specimen provided by the second illumination light alone and to acquire a third image which is an image of the specimen provided by the third illumination light alone, wherein the first image includes first optical information, the second image includes second optical information, and the third image includes third optical information, respectively,
an optical information recorder which records the first optical information, the second optical information, and the third optical information; and
a controller comprising hardware, the controller being configured to:
   compare the first image, the second image, and the third image with each other, and extract a first image identical-point originated pixel as an identical-point originated pixel in the first image, a second image identical-point originated image as an identical-point originated image in the second image, and a third image identical-point originated pixel as an identical-point originated pixel in the third image, which are originated from an identical point at three or more positions on the specimen, in association with each other, the identical-point originated pixel extracting circuit extracts a first identical point and a second identical point as identical points on the specimen; and
compare first optical information which is first light volume information of the specimen based on the first illumination light, detected from a first image first identical-point originated pixel at the first identical point at the three or more positions, second optical information which is second light volume information of the specimen based on the second illumination light, detected from a second image first identical-point originated pixel, and third optical information which is third light volume information of the specimen based on the third illumination light, detected from a third image first identical-point originated pixel,
compare first optical information which is first light volume information of the specimen based on the first illumination light, detected from a first image second identical-point originated pixel at the second identical point at the three or more positions, second optical information which is second light volume information of the specimen based on the second illumination light, detected from a second image second identical-point originated pixel, and third optical information which is third light volume information of the specimen based on the third illumination light, detected from a third image first identical-point originated pixel, and
in all of the first identical point and the second identical point on the specimen, calculate light volume ratio information which is a ratio of the first light volume information of the first image J-th identical-point originated pixels and the second light volume information of the second image J-th identical-point originated pixels, where J is an integer which is 1 or more, and, when pixels, the light volume ratio information of which are substantially equal, are determined as equal light volume ratio pixels, and when the first and second images include a plurality of equal light volume ratio pixels, calculate, on the basis of magnitudes of the light volume information of the equal light volume ratio pixels, specimen perspective information which is a relative distance relationship from the image sensor;
estimate a surface shape of the specimen on the basis of the specimen perspective information; and
display a stereoscopic image based on the estimated surface shape.

* * * * *